(12) United States Patent
Duncan et al.

(10) Patent No.: US 9,101,454 B2
(45) Date of Patent: Aug. 11, 2015

(54) CERVICAL SPINE STABILIZING SYSTEM (75) Inventors: William David Duncan, Kirkland, WA (US); Roderick A. Hyde, Redmond, WA (US)

(73) Assignee: Elwha LLC, Bellevue, WA (US)

( * ) Notice: Subject to any disclaimer, the term of this patent is extended or adjusted under 35 U.S.C. 154(b) by 375 days.

(21) Appl. No.: 13/464,044

(22) Filed: May 4, 2012

(65) Prior Publication Data
US 2013/0296755 A1 Nov. 7, 2013

(51) Int. Cl.
*A61F 5/00* (2006.01)
*A61F 5/058* (2006.01)
*A61F 5/055* (2006.01)
*A63B 71/12* (2006.01)
*A42B 3/04* (2006.01)
*A61F 13/12* (2006.01)

(52) U.S. Cl.
CPC .............. *A61F 5/05883* (2013.01); *A42B 3/04* (2013.01); *A61F 5/055* (2013.01); *A61F 5/0585* (2013.01); *A61F 13/12* (2013.01); *A63B 71/12* (2013.01)

(58) Field of Classification Search
CPC .................................. A61F 5/055; A42B 3/04
USPC .................... 2/455, 410, 422; 602/1, 5, 18
See application file for complete search history.

(56) References Cited

U.S. PATENT DOCUMENTS

| | | | |
|---|---|---|---|
| 5,599,290 A | 2/1997 | Hayes et al. | |
| 5,624,727 A * | 4/1997 | Stoy | 428/76 |
| 6,701,529 B1 | 3/2004 | Rhoades et al. | |
| 6,931,669 B2 | 8/2005 | Ashline | |
| 7,155,747 B2 | 1/2007 | Baker | |
| 7,226,878 B2 | 6/2007 | Wagner et al. | |
| 7,498,276 B2 | 3/2009 | Wagner et al. | |
| 7,789,844 B1 * | 9/2010 | Allen | 602/20 |
| 2003/0088906 A1 | 5/2003 | Baker | |
| 2004/0255368 A1 | 12/2004 | Baker | |
| 2005/0015859 A1 | 1/2005 | Ashline | |
| 2005/0027222 A1 | 2/2005 | Harty | |
| 2006/0234577 A1 | 10/2006 | Wagner et al. | |
| 2007/0149079 A1 | 6/2007 | Vito et al. | |
| 2007/0186329 A1 | 8/2007 | Baker | |
| 2007/0245464 A1 | 10/2007 | Baker | |
| 2008/0146981 A1 | 6/2008 | Greenwald et al. | |
| 2008/0172779 A1 | 7/2008 | Ferguson | |
| 2008/0256684 A1 | 10/2008 | Ashline | |
| 2008/0313791 A1 | 12/2008 | Nagely | |
| 2009/0191989 A1 | 7/2009 | Lammer et al. | |
| 2010/0192290 A1 | 8/2010 | Husain | |
| 2010/0286581 A1 * | 11/2010 | Hipp et al. | 602/18 |
| 2011/0185481 A1 | 8/2011 | Nagely et al. | |

OTHER PUBLICATIONS

PCT International Search Report; International App. No. PCT/US2013/039382; Oct. 8, 2013; pp. 1-2.

(Continued)

*Primary Examiner* — Alireza Nia
*Assistant Examiner* — Tarla Patel
(74) *Attorney, Agent, or Firm* — Suiter Swantz pc llo (57) ABSTRACT

A passive cervical spine stabilizing system includes a head engagement member, a torso supported member, and at least one stabilization connector having a first portion configured to be secured to the head engagement member and having a second portion configured to be secured to the torso supported member, wherein the at least one stabilization connector includes a surface in contact with a shear-thickening non-Newtonian fluid.

56 Claims, 7 Drawing Sheets

(56) References Cited

OTHER PUBLICATIONS

"Pro-Neck-Tor, How It Works", http://www.pronecktor.com/index.php?section=works, Aug. 24, 2012.

Lauren Gravitz, "A Helmet to Prevent Paralysis—Technology Review", http://www.technologyreview.com/news/417015/a-helmet-to-prevent-paralysis/, Aug. 24, 2012.

* cited by examiner

CERVICAL SPINE STABILIZING SYSTEM

BACKGROUND

Systems and materials are described to prevent injury from impact, shock, jarring motion, and the like. Certain systems and materials include rheological fluids activated by magnetic or electronic control.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

The neck, including the cervical spine, is one of the most critical and delicate human body parts. Modern medicine has long recognized the need for protecting, preventing, treating, and rehabilitating neck injuries.

Embodiments of the cervical spine stabilizing system described herein can be used in numerous sports or other activities, such as in horse riding, football, or other sports where a helmet can be used. Additionally, the system can be used therapeutically, medically, or for physical fitness, such as in rehabilitation, physical therapy, or resistive weight training.

The system can include links between a helmet and a shoulder or torso harness. The system can provide protection by absorbing the energy of impacts. The system can use high-shear materials arranged between surfaces in the device, wherein the high-shear materials can move through a high-shear fluid, such as a shear-thickening non-Newtonian fluid, or induce shear in a fluid, which can include a shear-thickening in a shear-thickening non-Newtonian fluid. This induction of shear or interaction of high-shear materials with the fluid can cause portions of the cervical spine stabilizing system to stiffen under high acceleration or shock but still allow for normal movement of the head, neck, or other parts of the body under normal conditions or under relatively low shear. Embodiments of the system can be passive in operation, wherein passive in operation means that the system operates by reacting to forces or stimuli external to the system. Other embodiments can use an active operation, such as switchable electro-rheological, magneto-rheological, or vibrational fluidized materials triggered by an accelerometer.

Shear-thickening non-Newtonian fluids can include a colloidal suspension of spherical, substantially spherical, or non-spherical small particulates in a stabilized suspension. Suitable shear-thickening non-Newtonian fluids can include polyethylene glycol (PEG), oxide or carbonate or kaolin particles in PEG or glycerin, dynamically linked polymers (e.g., Poly Dimethyl Siloxane), thickening agents such as water heavily loaded with corn starch or corn flour, sugar water mixtures, potassium silicate in water, polymethyl methacrylate (PMMA) particles in PEG, carbon black in oil/tetradecane ($C_{14}H_{30}$) fluid, or alumina particles in oil/tetradecane fluid. Additional, suitable shear-thickening non-Newtonian fluids can include at least one water-swellable material (such as a clay) dispersed in an oil-external emulsion. The emulsion can include liquid oil, an oil-soluble surfactant, and aqueous-phase droplets containing a dissolved polymer. For example, the liquid oil can be a low-viscosity, paraffinic oil such as mineral oil, and the oil-soluble surfactant can be added to stabilize the aqueous-phase droplets and to prevent premature mixing with clay particles during low shear rate events. The polymer dissolved in the aqueous phase can include polyacrylamide. The polymer can react with clay after high shear rate mixing to form a higher-strength paste than the clay alone. The increased strength results from a crosslinking of water-swollen clay particles by the polymer.

The system described herein can allow for a normal range of motion of the head or neck; however, the portions of the system can become stiffened under rapid or excessive movement of the head or neck relative to the body.

Embodiments of the system can allow for the degree of protection provided by the cervical spine stabilizing system to be controlled or adjusted by a user, an integrated or external computing device, an operator, a medical professional, a therapist, a caretaker, or other individual. The system can include an integrated computing device for controlling, adjusting, or calibrating the system before, during, in real time, or after an activity. The computing device can communicate data over a wired or wireless network with other computing devices to assist in controlling, adjusting, or calibrating a particular user's system or other users' systems. The computing device of the system can optionally include a recording mechanism to record data, such as impact data, stress data, strain data, tension force data, position data, range of motion data, or other data. The recording mechanism can include a volatile memory or non-volatile memory. The computing device can include a transmitter configured to send data over a wireless network. Likewise, the computing device can include a receiver configured to receive data over a wireless network. Accordingly, the computing device can dynamically control, adjust, or calibrate the system according to stored data, user profile data, activity profile data, system configuration data, program output data, recorded data, sensor data, extrapolated or interpolated data, computed data, single or multi-variable linearly regressed data, received data, network data, connected-computer data, or other data.

Also, the degree of protection can be statically or dynamically adjusted, calibrated, controlled, or customized to suit particular user needs. The system can be statically or dynamically adjusted, calibrated, controlled, or customized for user needs, including age, weight, activity, disability, strength, body mass index, gender, or the like. For example, adjustment, calibration, control, or customization to suit particular needs can include controlling the system or modifying the structure of the system.

The degree of protection can be controlled or adjusted by modifying or selecting one or more particular fluids to be used in the system. Modifying the fluid can effect changes to fluid properties. For example, fluid modification can include increasing or decreasing the amount of a particular fluid, increasing or decreasing the pressure of a particular fluid, purging or draining or evacuating a particular fluid, injecting or introducing a particular fluid, increasing or decreasing the concentration of a particular fluid, dissolving, suspending, or interspersing an additive in the fluid, adding a reactant to a particular fluid, increasing or decreasing fluid temperature, or the like.

The degree of protection can be controlled or adjusted by modifying the structure of the system. Modifying the structure can include fitting, adjusting, or interchanging components to accommodate a particular activity, conditions, or body type. Modifying the structure of the cervical spine stabilizing system can further include: adding or removing stabilization connectors; repositioning stabilization connectors; shortening or lengthening stabilization connectors; adding or removing elongated reservoirs to one or more stabilization connectors; altering the arrangement of stabilization connectors; altering the arrangement of elongated reservoirs within a particular stabilization connector; adding or removing one or more shear devices to one or more stabilization connectors, repositioning a particular shear device within an elongated reservoir; tightening or loosening a particular shear device; attaching or detaching one or both ends or other attachment points of a particular shear device; adding or removing constant frequency or variable frequency fluid vibrator or agitator units; adding or removing accelerometers; opening or closing valves, such as solenoid valves; adding or removing heating or cooling units; adding or removing thermal insulation material; adding or removing fluid pressure adjusting units; controllably activating or deactivating artificial muscle; adding or removing single-direction or multi-direction pump units; or otherwise adding, removing, adjusting, calibrating, or rearranging said or similar system components.

An embodiment of the cervical spine stabilization system can include a an integrated or external computing device configured to dynamically control, activate, deactivate, increase, decrease, amplify, reduce, rearrange, adjust, or calibrate said or similar system components or outputs of said or similar system components based upon system data, including data received from sensors, a recording mechanism, an associated program or application, a storage device, a receiver, via a network, or the like. The integrated or external computing device may be linked and/or operatively coupled to said or similar system components, as well as sensors, a receiver, a transmitter, a network, a computing device, other components, or the like.

In an embodiment, the degree of protection can be controlled or adjusted according to user or activity needs by vibrating fluid or fluids used in the cervical spine stabilizing system. This fluid vibration can change the fluid properties of a particular fluid or fluids, such as shear-thickening non-Newtonian fluids. The system, such as by an integrated computing device, can control the occurrence of and amount of fluid vibration by activating, deactivating, or variably controlling a vibration mechanism, such as a fluid vibrator or agitator unit, which can include a constant or variable speed electric motor with an off-centered or centered center of mass about the motor's axis.

In an embodiment, the degree of protection can be controlled or adjusted according to user or activity needs by incorporating artificial muscle. For example, artificial muscle can include linear compliant elements which undergo reversible length changes in response to stimuli, such as chemical stimuli, electrical stimuli, or magnetic stimuli. For example, one or more stabilization connectors can include artificial muscle. An integrated or external computing device can be configured to stimulate or send a signal to effect a stimulus in the artificial muscle. In response to the stimulus or the signal to effect the stimulus, the artificial muscle will react by shortening or lengthening so as to accommodate particular user or activity requirements. By way of example, stimulating the artificial muscle included as part of a stabilization connector may result in the artificial muscle contracting so as to accommodate an activity which requires a reduced range of neck motion. Artificial muscle can include the use of electroactive polymers (EAPs). Some EAPs suitable for artificial muscle include ferroelectric polymers (such as polyvinylidene fluoride), electrostrictive graft polymers, ionic EAPs (such as conductive polymers and ionic polymer-metal composites (such as Nafion, a sulfonated tetrafluoroethylene based fluoropolymer-copolymer (perfluorinated sulfonic acid) and Flemion, a perfluorinated carboxylic acid)), dielectric polymer EAPs, or gels (such as ionic gel electrodes sandwiching carbon nanotubes contained in an ionic fluid). Artificial muscle can also include electrically powered artificial muscle including carbon nanotube aerogel sheets (detailed in Aliev et al., *Science*, Vol. 232 March 2009, 1575-1578). EAPs can be electrically activated over a range of voltages (including low and high voltages) and a range of power (including low and high power). For example, the ionic based polymers can be activated with low voltages, whereas a dielectric polymeric class of EAPs generally requires large activation voltages but low power.

The degree of protection can also be controlled or adjusted according to user or activity needs by dynamically applying additional forces or torques to the fluid, such as through gas pressure, electromagnetic waves, mechanical force, stored chemical energy, heat, electromagnetic energy, or the like. Additionally, the degree of protection can be controlled or adjusted according to user or activity needs by adding electro-rheological or magneto-rheological fluids and providing a current or field.

The degree of protection can be controlled or adjusted according to user or activity needs by adding a stimulus. The stimulus can be dynamically controlled or applied. The stimulus can control or adjust the degree of protection associated with fluid vibration, shear-thickening non-Newtonian fluids, electro-rheological or magneto-rheological fluids, current inducers, field inducers, accelerometers, artificial muscles, pressurizers, pumps, agitators, heating units, cooling units, power sources, motors, braces, ratchets, locking-mechanisms, valves, such as solenoid valves, or the like. The stimulus can be controlled by an integrated or external computing device.

The system can include one or a plurality of sensors, such as sensors for measuring force, shock, acceleration, speed, strain, stress, position, orientation, air pressure, fluid pressure, tension, compression, torque, temperature, fluid turbidity, viscosity, or the other quantitatively measured physical, electromagnetic, or chemical qualities or properties. Each component of the system can include one or a plurality of sensors. The sensors can provide real time data feedback to the computing device. Each component of the system can be operatively connected to another component of the system and or the computing device; for example, the computing device can be linked or operatively coupled to sensors, a recording mechanism, a removable or non-removable storage device, a receiver, a transmitter, a network, or the like. The computing device can record, interpret, analyze, synthesize, and/or react to the sensor data. The sensor data can be used for dynamically and variably controlling, calibrating, or adjusting the system, associated structures, associated components, associated stimuli, or the like.

The cervical spine stabilizing system can be configured to or can restrict further substantial motion after a shear-thickening event. The system can include a mechanism, such as a ratchet or locking mechanism to restrict further motion after the shear-thickening event. The mechanism can be controlled by a computing device to control restriction of motion or release of restriction of motion. For example, the mechanism can be released upon command, time-out, sensor-input (e.g., current load or the like), and omission of sensor input. The mechanism can allow for motion only for a selected range of accelerations, forces, speeds, rates, profiles, or the like.

An embodiment of the cervical spine stabilizing system can comprise a passive cervical spine stabilizing system. The passive cervical spine stabilizing system can include a head engagement member; a shoulder or torso supported member; at least one stabilization connector; at least one fluid-filled container or reservoir; and one or more shear-thickening non-Newtonian fluids. The head engagement member can be attached to protective head equipment or can comprise part of protective head equipment. The head engagement member can operatively fit to a user's head such that the head engagement member can support tensile, compressive, or torsional forces without the head slipping. The at least one stabilization connector can be secured to one or both of the head engagement member and the shoulder or torso supported member. The at least one stabilization connector can be flexible or semi-rigid and can provide one or both of tensile or compressive resistance. The one or more fluid-filled containers or reservoirs can contain particular shear-thickening non-Newtonian fluids. The one or more fluid-filled containers or reservoirs can be attached to or contained within the head engagement member or shoulder or torso supported member. Additionally, the one or more fluid-filled containers or reservoirs can be contained within the stabilization connectors. The fluid-filled containers or reservoirs can be flexible or semi-rigid and can be comprised of tubes of suitable varying or constant cross-sectional area as a function of length.

Fluid-filled containers or reservoirs can include one or more internal shearing structures, such as shear devices, which can move relative to a shear-thickening non-Newtonian fluid or relative to other internal shearing structures or shear-inducing surfaces of a fluid-filled container or reservoir. The shear devices can be configured to undergo at least one of linear motion or angular motion. The shear devices can be connected to the stabilization connectors. A connection of a shear device to the stabilization connectors can comprise a mechanism configured to amplify motion of the shear device, convert linear motion of the stabilization connector to angular motion of the shear device, or convert angular motion of the stabilization connector to linear motion of the shear device. Shear slip can be avoided or controlled by utilizing surface roughening or texturing of shear device surfaces and/or internal surfaces of a fluid-filled container or reservoir.

Figure 1:
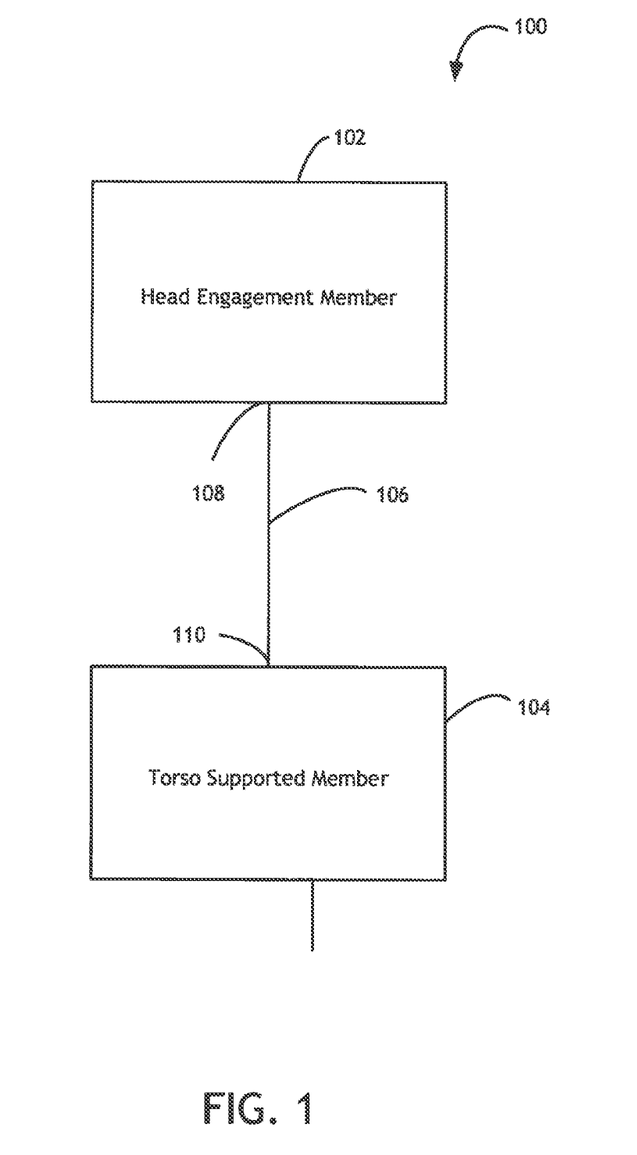
FIG. 1 shows a schematic diagram of a cervical spine stabilizing system.

FIG. 1 illustrates an embodiment of a cervical spine stabilizing system 100. In the embodiment of FIG. 1, the cervical spine stabilizing system 100 includes a head engagement member 102, a torso supported member 104, and a stabilization connector 106 between the head engagement member 102 and the torso supported member 104. The head engagement member 102 can be generally configured to engage at least a portion of a head region of a body. The torso supported member can be generally configured to engage at least a portion of a torso region of a body. The stabilization connector 106 can include a first portion 108 that is configured to be secured to the head engagement member 102, and can include a second portion 110 that is configured to be secured to the torso supported member 104. The stabilization connector 106 can also include a surface in contact with a shear-thickening non-Newtonian fluid. In order for the cervical spine stabilizing system 100 to provide protection to an individual, the shear-thickening non-Newtonian fluid can include a fluid property that is altered in response to a motion. As described herein, the shear-thickening non-Newtonian fluid can respond to the motion to provide stability to the stabilization connector 106 between the head engagement member 102 and the torso supported member 104.

In certain embodiments, the cervical spine stabilizing system 100 is configured to permit normal motion of the head, and is configured to protect the cervical spine and associated musculature, tendons, and ligaments of an individual from rapid and/or excessive movement of the head relative to the body. In certain embodiments, the cervical spine stabilizing system 100 is configured to provide a mechanism to strengthen neck muscles, such as through therapeutic usage. In certain embodiments, the cervical spine stabilizing system 100 is configured to provide protection from impacts to the cervical spine by providing a barrier between the cervical spine and the impact source.

Figure 2:
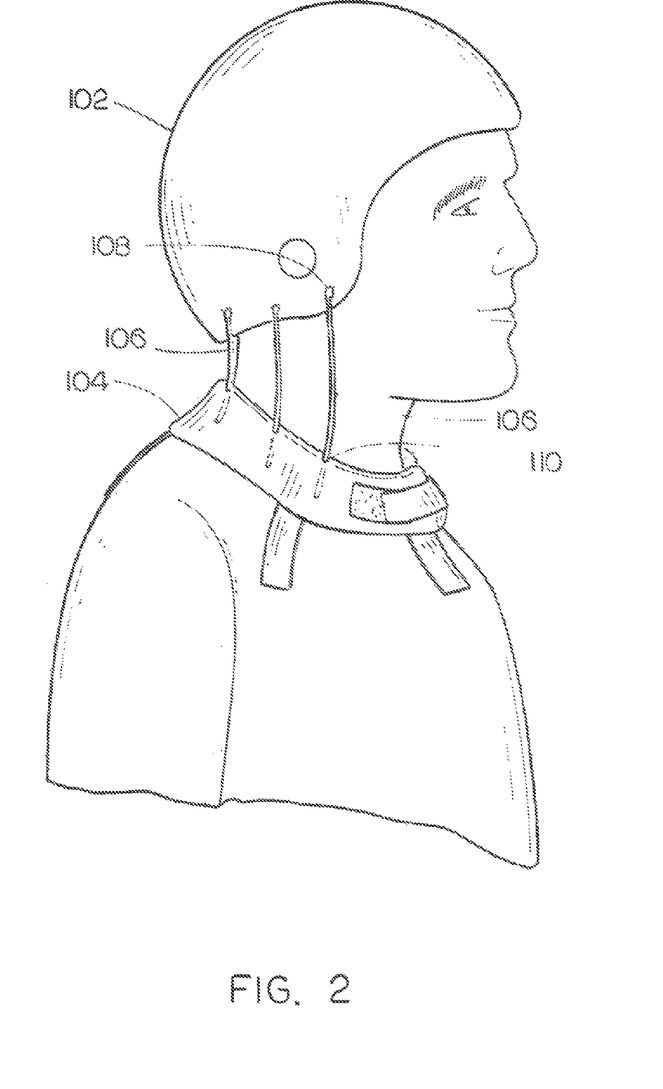
FIG. 2 depicts a diagrammatic view of an embodiment of a cervical spine stabilizing system including a reservoir in a torso supported member.
Figure 3:
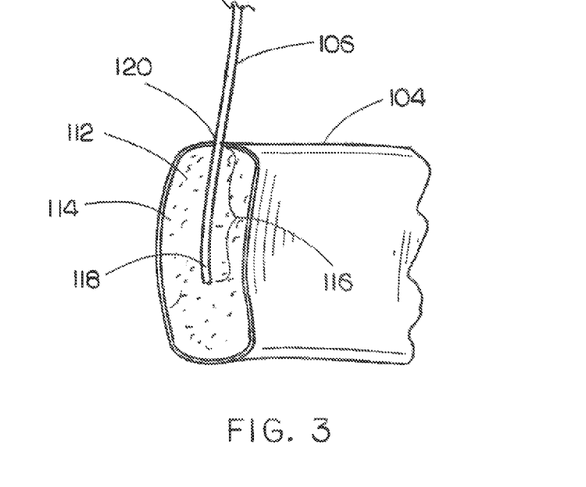
FIG. 3 depicts a diagrammatic partial cross-sectional view of the reservoir of FIG. 2.

FIGS. 2 and 3 depict an embodiment of the cervical spine stabilizing system 100 in which the torso supported member 104 defines a reservoir 112 configured to contain a shear-thickening non-Newtonian fluid 114. In the embodiment of FIGS. 2 and 3, the stabilization connector 106 includes a structural member extending from the first portion of the stabilization connector 106 to the second portion of the stabilization connector 106, such that the stabilization connector 106 forms a continuous structural element between the head engagement member 102 and the torso supported member 104. The stabilization connector 106 can include a region 116 configured to extend into the reservoir 112 to provide a surface 118 in contact with the shear-thickening non-Newtonian fluid 114. The cervical spine stabilizing system 100 can be configured to permit movement of the head engagement member 102 relative to the torso supported member 104, where the stabilization connector 106 does not substantially inhibit movement under normal conditions (i.e., those conditions under which the shear-thickening non-Newtonian fluid 114 is not activated). Movement of the head engagement member 102 relative to the torso supported member 104 can result in corresponding movement of the stabilization connector 106 relative to the reservoir 112, which can include movement of the surface 118 relative to the shear-thickening non-Newtonian fluid 114 within reservoir 112. Such movement of the surface 118 relative to the shear-thickening non-Newtonian fluid 114 can be sufficient to activate the shear-thickening non-Newtonian fluid 114 to alter the fluid property, depending on the composition of the shear-thickening non-Newtonian fluid 114, the resultant force of the movement, and the like.

In some embodiments, motion activation of the shear-thickening non-Newtonian fluid can be effected in response to a threshold range of motion. Additionally, motion activation of the shear-thickening non-Newtonian fluid can be effected in response to a threshold change in a position or an orientation of the head or neck relative to the torso-supported member. Also, motion activation of the shear-thickening non-Newtonian fluid can be effected in response to a threshold change in velocity or angular velocity respective to a position or an orientation of the head or neck relative to the torso-supported member. Motion activation of the shear-thickening non-Newtonian fluid can be effected in response to a threshold change in acceleration or angular acceleration respective to a position or an orientation of the head or neck relative to the torso-supported member. Further, motion activation of the shear-thickening non-Newtonian fluid can be effected in response to a certain type of motion. The amount of the surface area in contact with the shear-thickening non-Newtonian fluid can depend on a forcefulness, degree, or intensity of motion.

The reservoir 112 can include an input port 120 through which the region 116 of the stabilization connector 106 can pass to an interior of the reservoir 112. The torso supported member 104, the head engagement member 102, or the reservoir can include a seal (not shown) configured to cover or seal at least a portion of the input port 120. For instance, the seal can be configured to conform to the shape of the stabilization connector 106 which passes through the input port 120, such as to mitigate the loss of fluid from the reservoir through the input port 120. The seal can include at least one of a self-healing material, a self-sealing material, a layer of material, a viscous material, a porous material, a liquid material, a wickable material, a closable window, or a valve, such as a one-way valve or a bladder valve.

Figure 4:
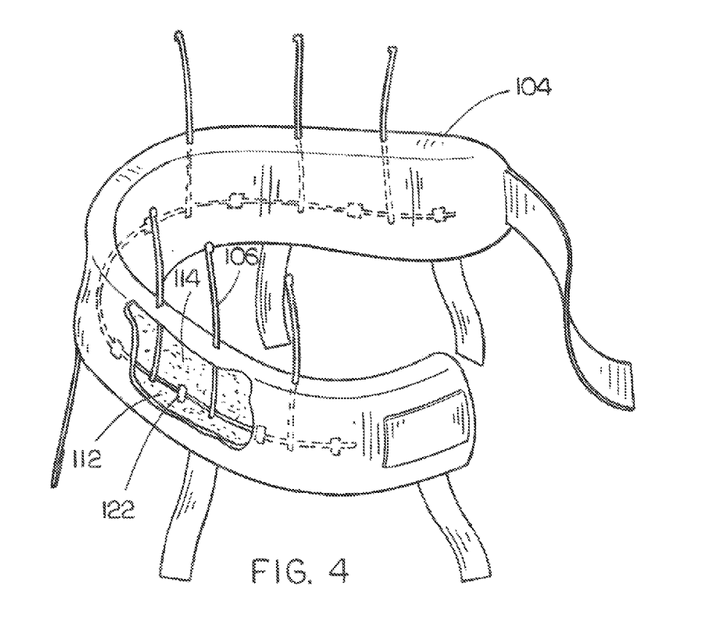
FIG. 4 depicts a diagrammatic view of an embodiment of a cervical spine stabilizing system including a shear device in a reservoir.

FIG. 4 depicts an embodiment of the cervical spine stabilizing system 100 in which the reservoir 112 includes a shear device 122 in contact with the shear-thickening non-Newtonian fluid 114 within the reservoir 112. The shear device 122 can comprise a structure configured to induce shear stress on the shear-thickening non-Newtonian fluid 114 in order to alter a fluid property of at least a portion of the shear-thickening non-Newtonian fluid 114 upon movement of the shear device 122. The fluid property can include viscosity, localized fluid binding properties, and the like. In the embodiment of FIG. 4, the shear device 122 is connected to the stabilization connector 106 within the reservoir 112. With the shear device 122 connected to the stabilization connector 106, movement of the stabilization connector 106 (e.g., via movement of the head engagement member 102 relative to the torso supported member 104) can cause the shear device 122 to move within the shear-thickening non-Newtonian fluid 114, imparting shear stress upon the shear-thickening non-Newtonian fluid 114. Such movement of the shear device 122 to alter a fluid property of at least a portion of the shear-thickening non-Newtonian fluid 114 depends on the composition of the shear-thickening non-Newtonian fluid 114, the resultant force of the movement, and the like.

In some embodiments, the reservoir can be contained within one or both of the head engagement member or the shoulder or torso supported member, wherein the reservoir can contain a plurality of chambers or sub-reservoirs. Each of the chambers or sub-reservoirs can contain a different non-Newtonian fluid having different properties. The chambers or sub-reservoirs can be configured or can be such that one or more of the stabilization connectors can engage with a particular non-Newtonian fluid of a particular chamber or sub-reservoir. Additionally, some of the chambers or sub-reservoirs can activate to only certain types of motion, motion in a particular direction, or particular degree of motion in a certain directions or types of motion. For example, the shear-thickening non-Newtonian fluid of a first group of chambers or sub-reservoirs can activate in response to forward or backward movement of the head relative to the torso; while a second group of sub-reservoirs or chambers can be configured such that the non-Newtonian fluid of the second group can activate only in response to a rotational movement of the head relative to the neck.

Figure 5:
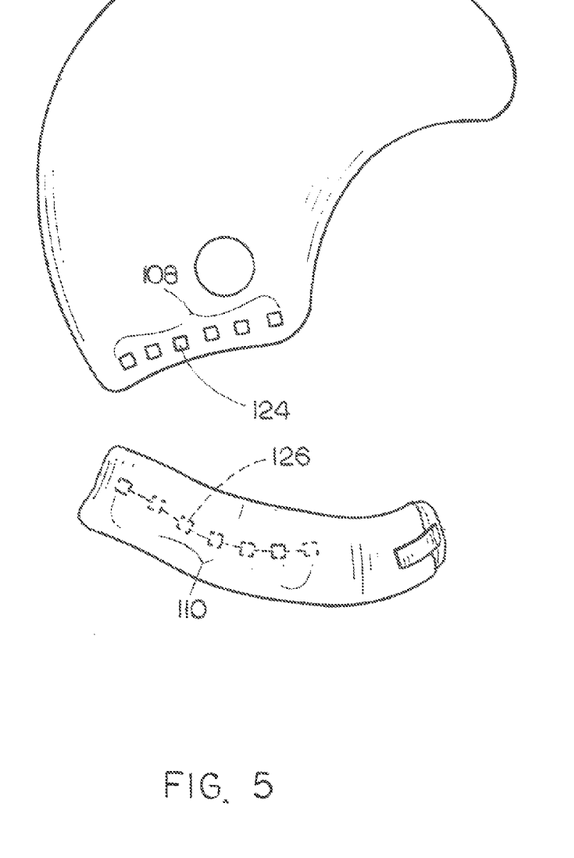
FIG. 5 depicts a diagrammatic view of an embodiment of a cervical spine stabilizing system including a magnetic coupling between a head engagement member and a torso supported member.

FIG. 5 depicts an embodiment of the cervical spine stabilizing system 100 in which the stabilization connector 106 provides a magnetic coupling between the head engagement member 102 and the torso supported member 104. In the embodiment of FIG. 5, the first portion 108 of the stabilization connector 106 includes a magnet 124 and the second portion 110 of the stabilization connector 106 includes a corresponding magnet 126. The magnet 124 can be coupled to the head engagement member 102, and the magnet 124 or the corresponding magnet 126 can provide the surface in contact with the shear-thickening non-Newtonian fluid 114. For instance, in the embodiment of FIG. 5, the corresponding magnet 126 is located within the reservoir 112 of the torso supported member 104. The reservoir 112 can contain a shear device 122 in an interior of the reservoir 112. The corresponding magnet 126 can be coupled to the shear device 122 such that movement of the head engagement member 102 relative to the torso supported member 104 can cause the magnetic coupling to induce movement of the corresponding magnet 126 and cause the shear device 122 to alter a fluid property of the shear-thickening non-Newtonian fluid 114.

Figure 6:
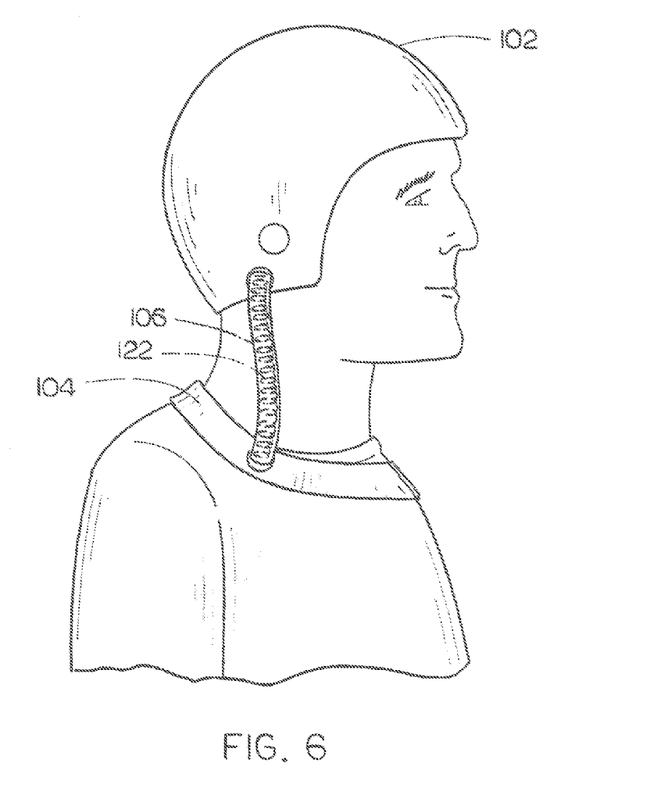
FIG. 6 depicts a diagrammatic view of an embodiment of a cervical spine stabilizing system including a reservoir contained within a stabilization connector.
Figure 7:
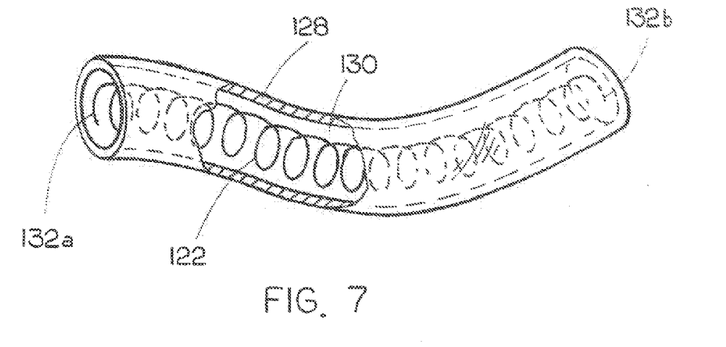
FIG. 7 depicts a diagrammatic partial view of the stabilization connector of FIG. 6.
Figure 8A:
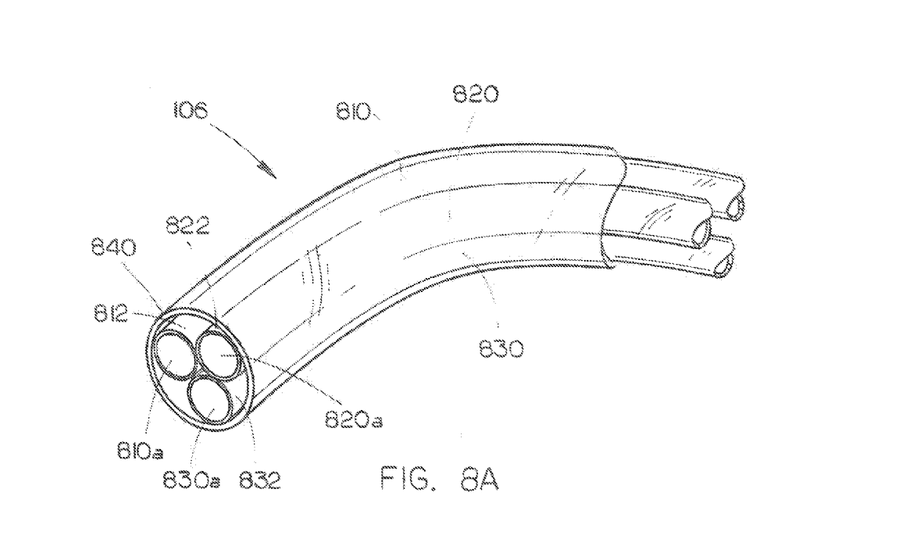
FIG. 8A depicts a diagrammatic partial view of an embodiment of a stabilization connector containing three elongated reservoirs.
Figure 8B:
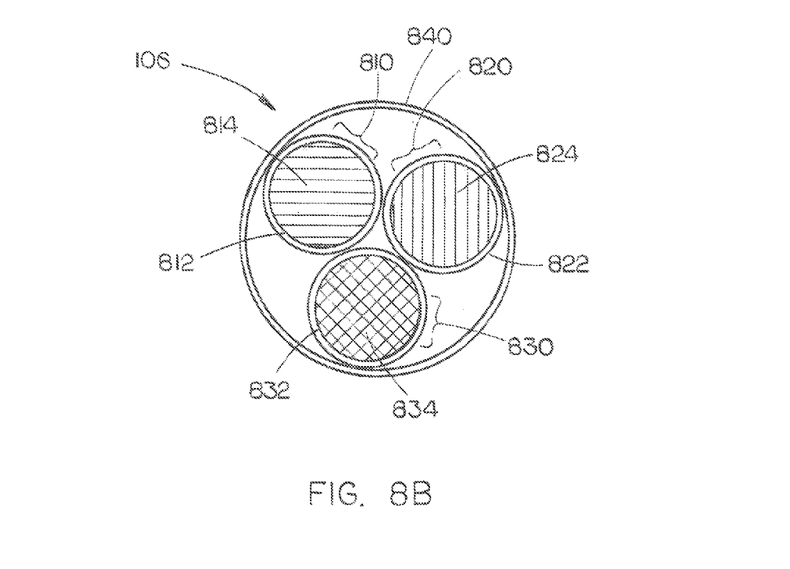
FIG. 8B depicts a diagrammatic cross-sectional view of an embodiment of a stabilization connector containing three elongated reservoirs.
Figure 8C:
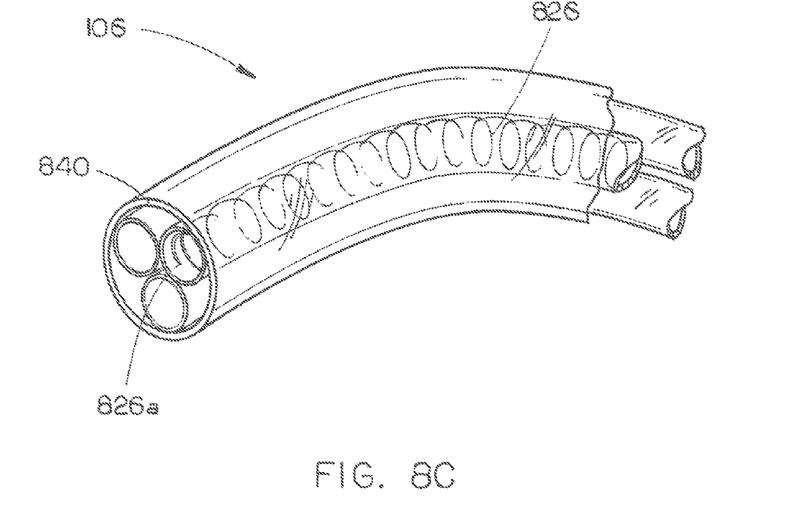
FIG. 8C depicts a diagrammatic partial view of an embodiment of a stabilization connector containing three elongated reservoirs with one shear device shown.
Figure 8D:
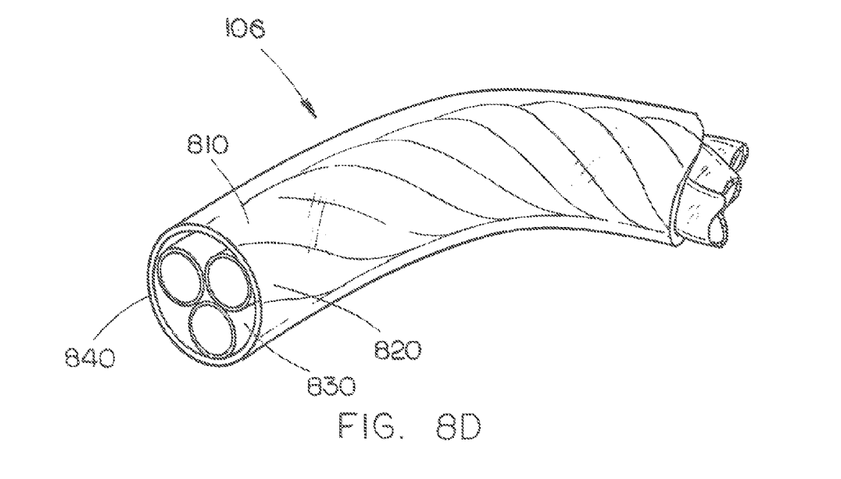
FIG. 8D depicts a diagrammatic partial view of an embodiment of a stabilization connector containing three elongated reservoirs arranged in a multi-helical configuration.

FIGS. 6 and 7 depict an embodiment of the cervical spine stabilizing system 100 in which the stabilization connector 106 includes a flexible or elastic material 128. Such material 128 can provide ease of movement of the head engagement member 102 relative to the torso supported member 104. In the embodiment of FIGS. 6 and 7, the stabilization connector 106 includes an elongated reservoir 130, wherein the elongated reservoir 130 contains the shear-thickening non-Newtonian fluid 114. The stabilization connector 106 can also include a shear device 122 within the elongated reservoir 130 such that movement of the head engagement member 102 relative to the torso supported member 104 can cause the shear device 122 to move within the elongated reservoir 130 to alter a fluid property of the shear-thickening non-Newtonian fluid 114, such as by imparting a shear force to the shear-thickening non-Newtonian fluid 114. The shear device 122 within the elongated reservoir 130 can include one or more ends coupled to a portion of the elongated reservoir 130. In the embodiment of FIGS. 6 and 7, a first end 132*a* of the shear device 122 is attached to a portion of the elongated reservoir 130 and a second end 132*b* is attached to another portion of the elongated reservoir 130, such that the shear device 122 is positioned throughout the elongated reservoir 130.

The stabilization connector 106 can include a protective exterior material, where the protective exterior material can include an accessibility element to permit access to an interior of the stabilization connector 106.

The first portion 108 of the stabilization connector 106 can be configured to be secured to the head engagement member 102 to permit a pivotable range of motion between the head engagement member 102 and the first portion 108. The first portion 108 of the stabilization connector 106 can be configured to be secured to the head engagement member 102 to permit a torque-limiting range of motion between the head engagement member 102 and the first portion 108. The second portion 110 of the stabilization connector 106 can be configured to be secured to the torso supported member 104 to permit a pivotable range of motion between the torso supported member 104 and the second portion 110. The second portion 110 of the stabilization connector 106 can be configured to be secured to the torso supported member 104 to permit a torque-limiting range of motion between the torso supported member 104 and the second portion 110. The stabilization connector 106 can include an adjustment member (not shown) configured to adjust a length of the stabilization connector 106.

FIGS. 8A, 8B, 8C, and 8D illustrate partial views and a cross-sectional view of implementations of a stabilization connector 106 of some embodiments of the cervical spine stabilizing system. A stabilization connector 106 can include a protective exterior material 840 and one or more elongated reservoirs (e.g., 810, 820, and 830). The protective exterior material 840 can include protective or thermal insulating qualities. The protective exterior material 840 can surround the one or more elongated reservoirs (e.g., 810, 820, and 830) and other internal components of a stabilization connector, such as sensors, electronics, wires, pump units, agitators, motors, vibration devices, accelerometers, solenoid valves, computing devices, or the like. The protective exterior material 840 can include an accessibility element, whereby the interior of the stabilization connector can be accessed for inspection, maintenance, or modification. The accessibility element of the protective exterior material 840 can be resealably accessed, such as through zippers, magnets, laces, buttons, clips, hooks, ties, hook-and-loop fabric, or the like. Some implementations of the accessibility element can resist moisture intrusion to internal portions of the stabilization connector.

The stabilization connector can include one or more elongated reservoirs (e.g., 810, 820, 830). The one or more elongated reservoirs can include reservoir walls which can contain the same or different shear-thickening non-Newtonian fluids and at least one shear device. The internal surfaces of the reservoir walls can also include physical features, such as porous surfaces, ridges (in an orientation lateral, perpendicular, or somewhere in between lateral and perpendicular to the lengthwise direction of the elongated reservoir), undulations, bumps, extended members, or the like, which enhance desired shear properties induced by a shear device. The reservoir walls can be non-porous and have flexible or elastic properties. The one or more elongated reservoirs can each contain the same or a different shear-thickening non-Newtonian fluid, whereby different shear-thickening non-Newtonian fluids have different physical properties, such as varying viscosity under varying shear ranges. Each of the elongated reservoirs can include one or more shear devices. As described above, the one or more shear devices can move within the elongated reservoir 130 to alter a fluid property of the shear-thickening non-Newtonian fluid 114 when a tensile or compressive force is exerted on the stabilization connector. The one or more shear devices can tend to return or return to a relaxed, neutral, or default position within the shear-thickening non-Newtonian fluid when compressive or tensile forces are reduced or cease to be exerted upon the stabilization connector.

The stabilization connector can further include bifurcated or multifurcated end portions or multiple attachment points for distributing net forces (i.e., tension, compression, or torsional forces) efficiently as force vectors concomitant to the bifurcated end portions or multiple attachment points to allow for efficient transfer of force, such as tension, between the stabilization connector and the shoulder or torso supported member or head engagement member. Vectorized forces can be distributed or transferred in multiple horizontal, vertical, or combinations of horizontal and vertical directions concomitant to the bifurcated or multifurcated ends or multiple attachment points. Bifurcated or multifurcated ends can include two or more ends. Each of the bifurcated or multifurcated ends or multiple attachment points can be capable of handling a different vectorized force component of a net force exerted on the stabilization connector. The bifurcated or multifurcated ends or multiple attachment points can join or converge at one or more ninety-degree, non-ninety-degree, acute, or obtuse angles. Converging point or points of the bifurcation or multifurcation of the stabilization connectors can be implemented within or outside of a reservoir. Each of the bifurcated or multifurcated ends or multiple attachment points can also include torque-limiting couplings or connectors for allowing the stabilizing connector to twist freely without getting tangled.

Each of one or more shear devices can be attached at both or one of a first end or a second end of the elongated reservoir. Also, one or more shear devices can be attached at non-end portions, such as the middle of the elongated reservoir. The one or more shear devices can be attached at multiple points in any combination of end or non-end portions of the elongated reservoirs for achieving desired effects. Both or one of a first end or a second end of the elongated reservoir or shear device can include a return device or can be connected to a return device for returning the shear device to a relaxed or neutral position. Further, the shear device itself can possess properties which allow it to tend to return or return to a relaxed or neutral position. The return device can include a spring, coil, rubber, latex, or other material having elastic properties or recoiling properties. Additionally, the return device can include the use of a mechanized, magnetic, or motorized return device. Alternatively, the shear device can be unconnected to either end or connected to some other portion or portions of the elongated reservoir.

The one or more shear devices of an elongated reservoir can include shear increasing elements distributed discretely or continuously along all of or desired portions of a shear device. The shear increasing elements can possess a physical attribute such that a portion of the shear device has a greater axial cross-sectional area or a greater surface-area-to-volume of the shear device at a location where a shear increasing element is located than at a location where the shear device lacks a shear increasing element. Shear increasing elements can further include the use of rough or porous surfaces along a shear device to increase friction or surface area between the shear device and the shear-thickening non-Newtonian fluid as the shear device moves through the shear-thickening non-Newtonian fluid. Each of the one or more shear devices can include a coil; a spring; or a rigid, non-rigid, or semi-rigid elongated member which can fit within the elongated reservoir. Additionally, the shear device can be elastic or inelastic. A first end of the shear device can be attached to the first end of the elongated reservoir and the second end of the coil or spring can be attached to the second end of the elongated reservoir. The shear device can include shear increasing elements, whereby the shear device includes any number of flaps, barbs, dangling members, paddles, fins, bumps, undulations, apertures, rough surfaces, porous surfaces, or the like along the shear device.

The herein described subject matter can illustrate different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, changes and modifications can be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, the convention (e.g., "a device having at least one of A, B, and C" would include but not be limited to devices that have A alone, B alone, C alone, A and B together, A and C together, B and C together, and/or A, B, and C together, etc.). In those instances where a convention analogous to "at least one of A, B, or C, etc." is used, in general such a construction is intended (e.g., "a device having at least one of A, B, or C" would include but not be limited to devices that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A passive cervical spine stabilizing system, comprising:
a head engagement member;
a torso supported member, including a reservoir, where the reservoir contains a shear-thickening non-Newtonian fluid; and
at least one stabilization connector having a first portion configured to be secured to the head engagement member and having a second portion configured to be secured to the torso supported member, wherein the at least one stabilization connector includes a surface in contact with the shear-thickening non-Newtonian fluid.

2. The system of claim 1, wherein the at least one stabilization connector is removably connected between the head engagement member and the torso supported member.

3. The system of claim 1, wherein the torso supported member or the head engagement member includes the reservoir.

4. The system of claim 3, wherein the at least one stabilization connector includes a structural member extending from the first portion to the second portion.

5. The system of claim 3, wherein at least a region of the first portion or the second portion is configured to extend into the reservoir to contact the shear-thickening non-Newtonian fluid.

6. The system of claim 5, wherein the reservoir includes an input port, wherein the at least a portion of the at least one stabilization connector is configured to pass through the input port into the reservoir.

7. The system of claim 6, wherein the torso supported member, the head engagement member, or the reservoir includes a seal covering at least a portion of the input port.

8. The system of claim 3, wherein the reservoir further contains a shear device in contact with the shear-thickening non-Newtonian fluid, the shear device configured to alter a fluid property of at least a portion of the shear-thickening non-Newtonian fluid upon movement of the shear device.

9. The system of claim 8, wherein the shear device is connected to the at least one stabilization connector.

10. The system of claim 9, wherein the connection comprises a mechanism configured to at least one of (i) amplify motion of the shear device, (ii) convert linear motion of the stabilization connector to angular motion of the shear device, or (iii) convert angular motion of the stabilization connector to linear motion of the shear device.

11. The system of claim 1, wherein the first portion of the stabilization connector includes a magnet.

12. The system of claim 11, wherein the second portion of the stabilization connector includes a corresponding magnet.

13. The system of claim 12, wherein the corresponding magnet of the second portion of the stabilization connector is connected to the surface in contact with the shear-thickening non-Newtonian fluid.

14. The system of claim 12, wherein the magnet of the first portion of the stabilization connector is connected to the surface in contact with the shear-thickening non-Newtonian fluid.

15. The system of claim 12, wherein the reservoir further contains a shear device in contact with the shear-thickening non-Newtonian fluid, the shear device configured to alter a fluid property of at least a portion of the shear-thickening non-Newtonian fluid upon movement of the shear device.

16. The system of claim 15, wherein the corresponding magnet is coupled to the shear device within the reservoir.

17. The system of claim 15, wherein the magnet is coupled to the shear device within the reservoir.

18. The system of claim 1, wherein the at least one stabilization connector includes an adjustment member configured to adjust a length of the at least one stabilization connector.

19. The system of claim 1, wherein the at least one stabilization connector further includes:
one or more reservoirs, wherein the one or more reservoirs contain one or more shear-thickening non-Newtonian fluids.

20. The system of claim 19, wherein the at least one stabilization connector includes one or more elongated reservoirs extending lengthwise within the at least one stabilization connector.

21. The system of claim 20, wherein the at least one stabilization connector includes a plurality of elongated reservoirs arranged in a substantially multi-helical configuration.

22. The system of claim 19, wherein the at least one stabilizing connector includes a plurality of reservoirs with at least one reservoir containing a shear-thickening non-Newtonian fluid different from a fluid of another reservoir of the plurality of reservoirs.

23. The system of claim 19, wherein at least one of the one or more reservoirs further contains a shear device, the shear device configured to alter a fluid property of at least a portion of the one or more shear-thickening non-Newtonian fluids upon movement of the shear device.

24. The system of claim 1, wherein the first portion of the at least one stabilization connector is unconnected to the head engagement member and the second portion is unconnected to the torso supported member, the at least one stabilization connector including a surface in contact with a shear-thickening non-Newtonian fluid.

25. The system of claim 1, wherein the amount of the surface area in contact with the shear-thickening non-Newtonian fluid depends on a forcefulness of motion.

26. The system of claim 1, wherein the first portion of the at least one stabilization connector is configured to be secured to the head-engagement member to allow for at least one of (i) a pivotable range of motion between the head-engagement member and the first portion of the at least one stabilization connector or (ii) a torque-limiting range of motion between the head-engagement member and the first portion of the at least one stabilization connector.

27. The system of claim 1, wherein the second portion of the at least one stabilization connector is configured to be secured to the torso-supported member to allow for at least one of (i) a pivotable range of motion between the torso-supported member and the second portion of the at least one stabilization connector or (ii) a torque-limiting range of motion between the torso-supported member and the second portion of the at least one stabilization connector.

28. The system of claim 1, wherein motion activation of the shear-thickening non-Newtonian fluid is effected in response to at least one of (i) a threshold range of motion, (ii) a threshold change in a position or an orientation of the head or neck relative to the torso-supported member, (iii) a threshold change in velocity or angular velocity respective to a position or an orientation of the head or neck relative to the torso-supported member, (iv) a threshold change in acceleration or angular acceleration respective to a position or an orientation of the head or neck relative to the torso-supported member, or (v) a certain type of motion.

29. A passive cervical spine stabilizing system, comprising:
a head engagement member;
a torso supported member, including a reservoir, where the reservoir contains a shear-thickening non-Newtonian fluid; and
at least one stabilization connector having a first portion secured to the head engagement member and having a second portion secured to the torso supported member, wherein the at least one stabilization connector includes a surface in contact with the shear-thickening non-Newtonian fluid.

30. The system of claim 29, wherein the at least one stabilization connector is removably connected between the head engagement member and the torso supported member.

31. The system of claim 29, wherein the torso supported member or the head engagement member includes the reservoir.

32. The system of claim 31, wherein the at least one stabilization connector includes a structural member extending from the first portion to the second portion.

33. The system of claim 31, wherein at least a region of the first portion or the second portion is configured to extend into the reservoir to contact the shear-thickening non-Newtonian fluid.

34. The system of claim 33, wherein the reservoir includes an input port, wherein the at least a portion of the at least one stabilization connector is configured to pass through the input port into the reservoir.

35. The system of claim 34, wherein the torso supported member, the head engagement member, or the reservoir includes a seal covering at least a portion of the input port.

36. The system of claim 31, wherein the reservoir further contains a shear device in contact with the shear-thickening non-Newtonian fluid, the shear device configured to alter a fluid property of at least a portion of the shear-thickening non-Newtonian fluid upon movement of the shear device.

37. The system of claim 36, wherein the shear device is connected to the at least one stabilization connector.

38. The system of claim 37, wherein the connection comprises a mechanism configured to at least one of (i) amplify motion of the shear device, (ii) convert linear motion of the stabilization connector to angular motion of the shear device, or (iii) convert angular motion of the stabilization connector to linear motion of the shear device.

39. The system of claim 29, wherein the first portion of the stabilization connector includes a magnet.

40. The system of claim 39, wherein the second portion of the stabilization connector includes a corresponding magnet.

41. The system of claim 40, wherein the corresponding magnet of the second portion of the stabilization connector is connected to the surface in contact with the shear-thickening non-Newtonian fluid.

42. The system of claim 40, wherein the magnet of the first portion of the stabilization connector is connected to the surface in contact with the shear-thickening non-Newtonian fluid.

43. The system of claim 40, wherein the reservoir further contains a shear device in contact with the shear-thickening non-Newtonian fluid, the shear device configured to alter a fluid property of at least a portion of the shear-thickening non-Newtonian fluid upon movement of the shear device.

44. The system of claim 43, wherein the corresponding magnet is coupled to the shear device within the reservoir.

45. The system of claim 43, wherein the magnet is coupled to the shear device within the reservoir.

46. The system of claim 29, wherein the at least one stabilization connector includes an adjustment member configured to adjust a length of the at least one stabilization connector.

47. The system of claim 29, wherein the at least one stabilization connector further includes:
one or more reservoirs, wherein the one or more reservoirs contain one or more shear-thickening non-Newtonian fluids.

48. The system of claim 47, wherein the at least one stabilization connector includes one or more elongated reservoirs extending lengthwise within the at least one stabilization connector.

49. The system of claim 48, wherein the at least one stabilization connector includes a plurality of elongated reservoirs arranged in a substantially multi-helical configuration.

50. The system of claim 47, wherein the at least one stabilizing connector includes a plurality of reservoirs with at least one reservoir containing a shear-thickening non-Newtonian fluid different from a fluid of another reservoir of the plurality of reservoirs.

51. The system of claim 47, wherein at least one of the one or more reservoirs further contains a shear device, the shear device configured to alter a fluid property of at least a portion of the one or more shear-thickening non-Newtonian fluids upon movement of the shear device.

52. The system of claim 29, wherein the first portion of the at least one stabilization connector is unconnected to the head engagement member and the second portion is unconnected to the torso supported member, the at least one stabilization connector including a surface in contact with a shear-thickening non-Newtonian fluid.

53. The system of claim 29, wherein the amount of the surface area in contact with the shear-thickening non-Newtonian fluid depends on a forcefulness of motion.

54. The system of claim 29, wherein the first portion of the at least one stabilization connector is configured to be secured to the head-engagement member to allow for at least one of (i) a pivotable range of motion between the head-engagement member and the first portion of the at least one stabilization connector or (ii) a torque-limiting range of motion between the head-engagement member and the first portion of the at least one stabilization connector.

55. The system of claim 29, wherein the second portion of the at least one stabilization connector is configured to be secured to the torso-supported member to allow for at least one of (i) a pivotable range of motion between the torso-supported member and the second portion of the at least one stabilization connector or (ii) a torque-limiting range of motion between the torso-supported member and the second portion of the at least one stabilization connector.

56. The system of claim 29, where motion activation of the shear-thickening non-Newtonian fluid is effected in response to at least one of (i) a threshold range of motion, (ii) a threshold change in a position or an orientation of the head or neck relative to the torso-supported member, (iii) a threshold change in velocity or angular velocity respective to a position or an orientation of the head or neck relative to the torso-supported member, (iv) a threshold change in acceleration or angular acceleration respective to a position or an orientation of the head or neck relative to the torso-supported member, or (v) a certain type of motion.

* * * * *